(12) United States Patent
Ballet et al.

(10) Patent No.: US 8,790,667 B2
(45) Date of Patent: Jul. 29, 2014

(54) SURFACE IMMOBILIZED CHAPERONES

(75) Inventors: Thomas Ballet, Baie-Mahault (FR);
Paolo Mangiagalli, Fontanil (FR)

(73) Assignee: Becton Dickinson France, Le Pont-de-Claix (FR)

( * ) Notice: Subject to any disclaimer, the term of this patent is extended or adjusted under 35 U.S.C. 154(b) by 0 days.

(21) Appl. No.: 13/582,840

(22) PCT Filed: Mar. 5, 2010

(86) PCT No.: PCT/IB2010/001113
§ 371 (c)(1),
(2), (4) Date: Nov. 15, 2012

(87) PCT Pub. No.: WO2011/107820
PCT Pub. Date: Sep. 9, 2011

(65) Prior Publication Data
US 2013/0156817 A1    Jun. 20, 2013

(51) Int. Cl.
*A61K 9/00* (2006.01)
*A61K 9/08* (2006.01)
*A61J 1/00* (2006.01)
*A61K 47/48* (2006.01)
*A61J 1/05* (2006.01)

(52) U.S. Cl.
CPC ... *A61J 1/00* (2013.01); *A61K 9/08* (2013.01); *A61K 9/0019* (2013.01); *A61K 47/48007* (2013.01); *A61J 1/05* (2013.01)
USPC ............................................ 424/400

(58) Field of Classification Search
None
See application file for complete search history.

(56) References Cited

FOREIGN PATENT DOCUMENTS

WO    0055183 A1    9/2000

OTHER PUBLICATIONS

Yang et al., Biosensors and Bioelectronlcs, 2003, 18, 311-317.*
BD Health Care Professional Services, "A Look at the Reuse of Insulin Needles", 2006, available online at: http://www.bd.com/us/diabetes/download/ Reuse_White_Paper.pdf.*
Rajan et al., Indian Journal of Pharm. Sciences, 2006, vol. 68, issue 5, 662-665.*
Yang et al., Biosensors and Bioelectronics, 2003, 18, 311-317, as in the ISR of the ISA dated Sep. 5, 2012.*
George et al., Detecting and exploring partially unfolded states of proteins using a sensor with chaperone bound to its surface, Biosensors & Bioelectronics, 2008, 963-969, 24.
Jhamb et al., Immobilized chaperones: A productive alternative to refolding of bacterial inclusion body proteins, Process Biochemistry, 2008, 587-597, 43.
Margulis et al., The characterization and use of different antibodies against the hsp70 major heat shock protein family for the development of an immunoassay, Electrophoresis, 1991, 670-673, 12.
Yang et al., Stabilization and re-activation of trapped enzyme by immobilized heat shock protein and molecular chaperones, Biosensors & Bioelectronics, 2003, 311-317, 18.

* cited by examiner

*Primary Examiner* — James H Alstrum Acevedo
*Assistant Examiner* — Kaipeen Yang
(74) *Attorney, Agent, or Firm* — The Webb Law Firm

(57) ABSTRACT

A container containing a therapeutic protein, characterized in that chaperones molecules are bound by a molecular linker to an inner surface of the container. The linker being interposed between the surface and the chaperone.

13 Claims, 5 Drawing Sheets

SURFACE IMMOBILIZED CHAPERONES

FIELD OF THE INVENTION

The present invention is directed to a container for a pharmaceutical compound having a protein component.

BACKGROUND OF THE INVENTION

Proteins are now commonly used in medical fields, and represent more than half of developed drugs. Insulin, albumin, interferon or antibodies are some examples.

A protein is a polypeptide chain with a particular folding, where the folding defines certain functions of the protein. However, this folding can be easily altered, for example, where the protein is unfolded or misfolded, by heat, extremes of pH, mechanical forces, chemical denaturants, by other proteins, or just by contact with surfaces of glass or plastic, for example. Proteins stored in medical containers like syringes, cartridges, vials, ampoules, bottles or test tubes can thus be entirely inactivated within several hours.

Unfolded proteins can aggregate and form insoluble blocks, whereas misfolded proteins can have unexpected and dangerous effects on human body, both of which are undesirable.

That is why control and prevention of unwanted unfolding or misfolding of therapeutic proteins is an important and ubiquitous hurdle to be addressed during the manufacture, storage, shipping, and administration of pharmaceutical products.

Methods have been proposed to solve this problem, most of them based on biological processes. In particular, it is known to use a class of large proteins named chaperones for assisting with the folding/unfolding and the assembly/disassembly of other macromolecular structures.

In most of these known methods, the chaperones are free in the pharmaceutical solution. They can thus contribute to the refolding of unfolded proteins in the solution. However it could be interesting to benefit from the function of the chaperones without releasing the chaperones free in solution.

International Patent Publication WO00/55183 discloses immobilizing chaperones on a solid surface. This document proposes to perform this immobilization by a chemical reaction which generates covalent bonds between the chaperone and the treated surface.

Such immobilization of the chaperones prevents their releasing free in solution, while still benefiting from their refolding effect.

However, as the chemical reaction involves thiols, the chaperone can be bound to a solid surface only by a disulfide. Disulfides of chaperones (and of proteins in general) form structural constraints necessary to keep them in their native conformation. Due to the formation of covalent bonds in the chemical reaction described in International Patent Publication WO00/55183, at least one disulfide bridge is destroyed and there is a risk for the chaperone not to remain in its native conformation and to loose its activity after such chemical modification.

Moreover, if the chaperone does not contain a disulphide, it cannot be bound.

It is a general object of the invention to improve known methods such as mentioned above. In particular, it is an object of the invention to prevent release of chaperones or fragments of chaperones in pharmaceutical solutions without altering their efficiency against protein unfolding. In addition, it is an object of the present invention to provide an improved container for a pharmaceutical compound having a protein component. The improved container according to the present invention is an improvement over known containers with respect to the inner surface coating of the container and its improved effect on a pharmaceutical compound having a protein component.

It is another object of the invention to provide a method which can apply to any chaperone.

SUMMARY OF THE INVENTION

The present invention aims to solve the above-identified shortcomings of the prior art by providing a container for a therapeutic protein. An inner surface of the container of the present invention is coated with chaperones coupled to the inner surface by a molecular linker—the linker being interposed between the surface of the container and the chaperone.

The present invention also provides a method for coating the inner surface of a container with chaperones, characterized in that it comprises the steps of:
  filling the container with a solution containing a molecular linker;
  emptying the container after a time of pre-adsorption of said molecular linker;
  washing the inner surfaces of the container with a buffer;
  adding to said inner surfaces the chaperones.

BRIEF DESCRIPTION OF THE DRAWINGS

The above, and other objects, features and advantages of this invention, will be apparent in the following detailed description of an illustrative embodiment thereof with is to be read in connection with the accompanying drawings wherein.

DETAILED DESCRIPTION OF THE INVENTION

Figure 1:
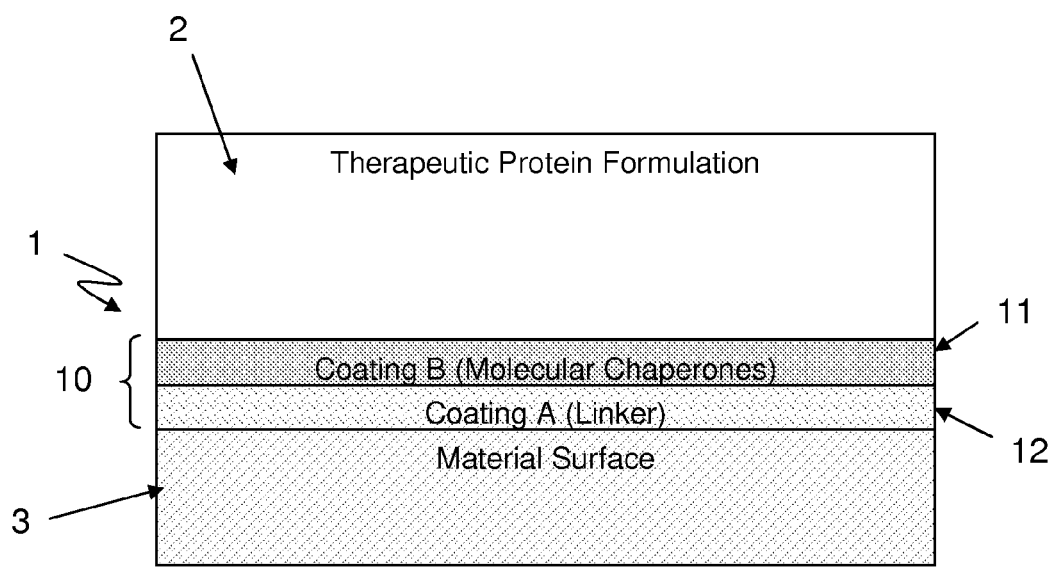
FIG. 1 is a schematic view of a transversal section of the surface of a container in accordance with the present invention.

FIG. 1 shows a schematic view of a cross-section of a surface of a container 1 according to the invention. As used herein, the term container shall refer to, by way of illustration and not limitation, a container suitable for holding any pharmaceutical solution. Examples of a container in accordance with the present invention include a syringe (with or without an attached needle), a cartridge, a vial, an ampoule, reservoir or other device or structure suitable for holding and containing a pharmaceutical compound, typically in liquid form, but not necessarily so. Other containers suitable for holding a pharmaceutical solution are also within the scope and spirit of the present invention. The container 1 is suitable for holding a pharmaceutical solution 2 that may be a liquid that may be in contact with the surface 3 of the container 1.

Figure 2:
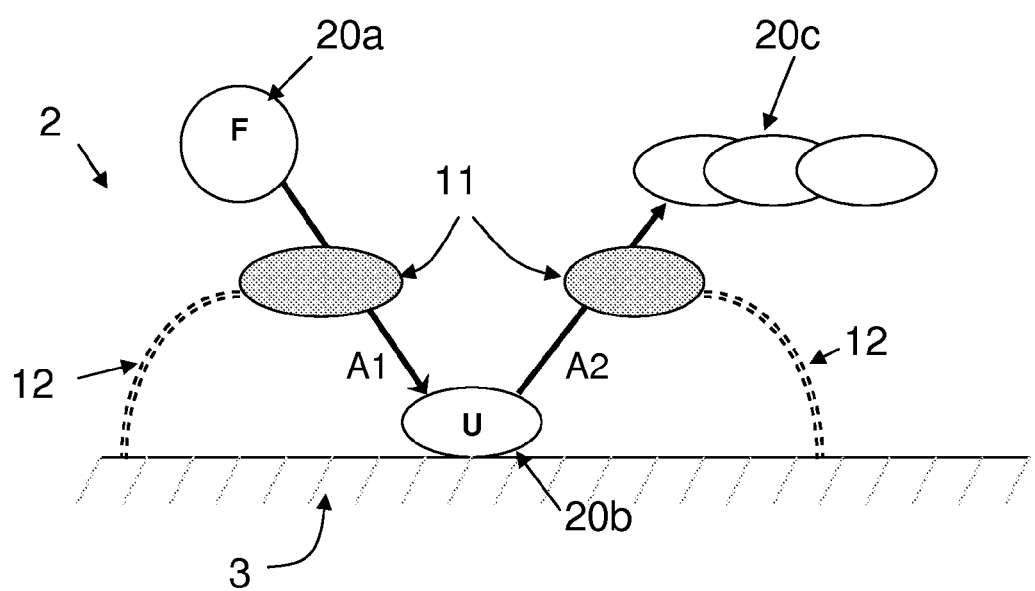
FIG. 2 is an enlarged schematic view of a coating according to the present invention, which explains mechanisms leading to proteins aggregation.

Between the solution 2 and the surface 3, is a coating 10. The coating 10 is made of two components and serves to isolate the surface 3 from the solution 2. A first component of the coating consists of molecular chaperones 11, which are bound to surface 3 by a molecular linker 12—a second component of the coating 10. Molecular linkers 12 may be formed as a layer on surface 3. For example, the linker 12 and chaperone 11 may have an interface defined between them, such as depicted in FIG. 2. Alternatively, the linker 12 and the chaperone 11 may have interpenetration or interphase between them, so that there may not be a clear delineation between the linker 12 and chaperone 11.

This molecular linker 12 is made of a single molecule, or of an agglomerate of several molecules. Indeed, in prior art, all the methods used for coupling polypeptides to solid surfaces involve direct chemical bonding after surface and/or protein modification by the mean of a chemical agent. Nothing in these known methods is interposed between the surface 3 and the chaperone 11—these chemical methods therefore do not imply any linker.

In the invention, the linker 12 is a molecule (such as proteins (e.g. antibodies), carbohydrates (polysaccharides) or any other biological polymers), preferably selected for its affinity with the chaperone 11 without leading to the modification of the chaperone 11. Therefore, this coupling does not involve any covalent chemical reaction, there is no contact between the material surface and the chaperone. The linker is interposed between them.

No specificities are required for the binding between the surface to be treated and the linker. The linker can be bound to the surface by hydrogen bonds (as in the case of a hydrophilic/hydrophobic linker), covalent bonds, Van der Waals interactions, as a few examples.

As represented in FIG. 2, the protein aggregation process typically consists of two steps (corresponding to the two arrows A1 and A2). As noted, protein aggregation is undesirable, and may result in dangerous changes to the pharmaceutical compound. Folded proteins 20a are therapeutic proteins in pharmaceutical solution 2. As it is known, the hydrophobicity of a material surface 3 such as siliconized glass or plastic induces unfolding of proteins 20a into unfolded proteins 20b. Unfolded proteins 20b are denatured and are conformationally altered proteins which have lost their primary shape.

Unfolded proteins 20b can then agglomerate and form solid blocks 20c which quickly grow.

Presence of traces of such insoluble aggregates 20c in a protein pharmaceutical preparation is generally unacceptable for the release of a pharmaceutical product.

However, the applicant noticed that if a siliconized medical glass container is filled with folded proteins, they will start to aggregate on the material surface only after a "lag-time".

During this lag-time, which can last several hours or even days, the amount of unfolded protein is increasing, while adsorption stays almost constant with a thin monolayer of proteins absorbed on the inner surfaces of the device. Imperfections of this layer are slowly forming nucleation sites, which then induce aggregation. Solid blocks of unfolded aggregated protein will grow on these sites from the end of the lag-time.

In a preferred embodiment, the unfolded proteins which are pre-adsorbed on the hydrophobic device surface are used as molecular linkers 12.

Indeed, a chaperone comprises a substrate binding domain containing a slot with an affinity for neutral, hydrophobic amino acid residues, which is the functional core of the chaperone for interaction with peptides. Thanks to this slot, a chaperone added before the end of the lag-time will bind to the adsorbed unfolded protein and will stabilize the layer of adsorbed unfolded proteins.

A high amount of energy is required to break the molecular linker or one of the bindings, so the release of the chaperone in solution is prevented. Further aggregation is also prevented thanks to the chaperones.

Figure 3:
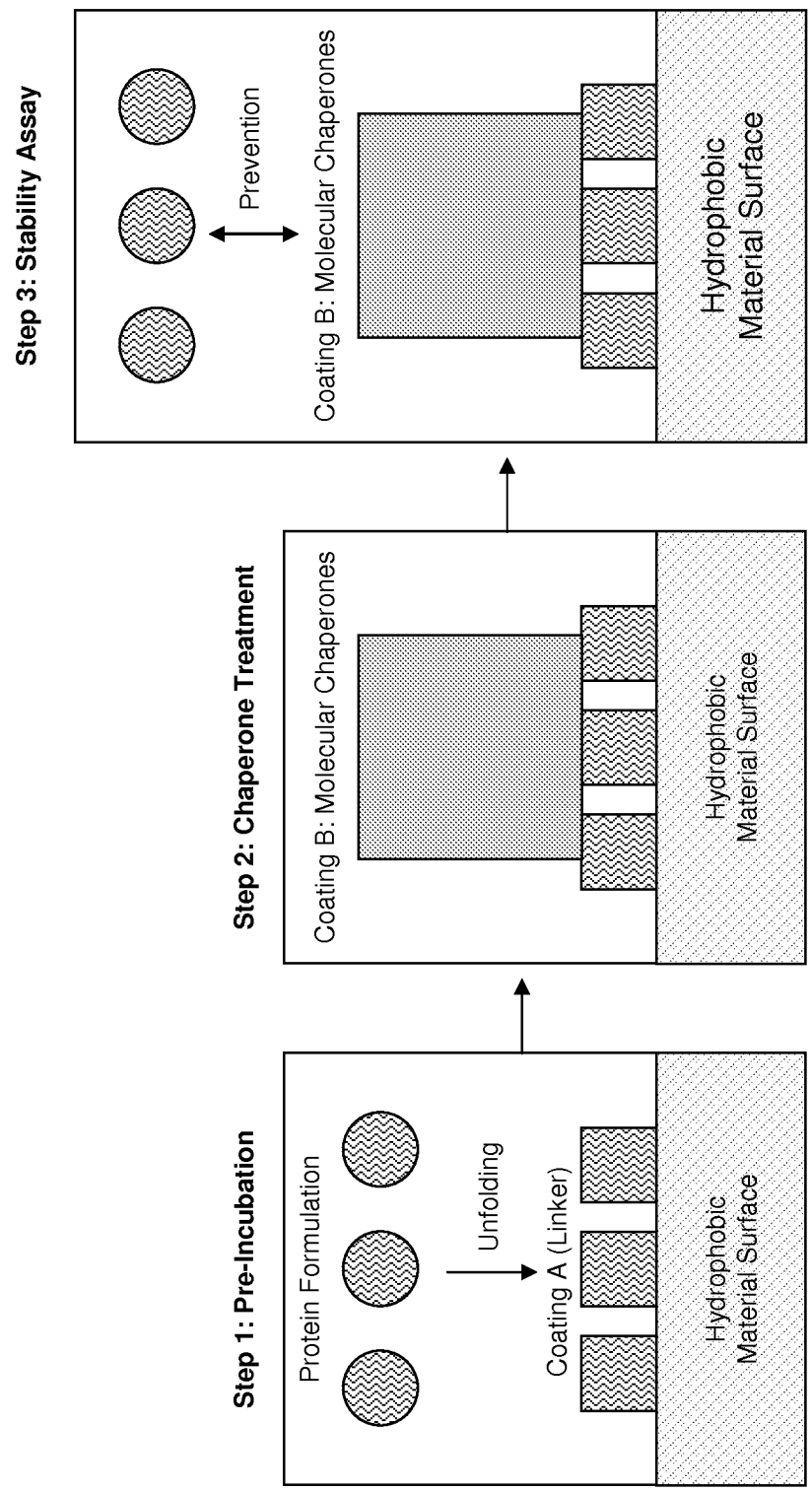
FIG. 3 represents schematically three steps of the process of coating of a container according to the invention.

As represented in FIG. 3, the present invention enables to avoid the nucleation and aggregation step by adding chaperone molecules before the end of the lag-time in order to neutralize the nucleation sites of the layer of unfolded proteins before the aggregation becomes unstoppable. When adsorbed, unfolded proteins are tightly bound to the material surface by hydrogen bonds, so they act as molecular linkers 12. The mono layer of unfolded protein forms the layer defined by the linkers 12.

Therefore, the molecular linker 12 is preferably selected in order to cover the entire surface with unfolded proteins and form an adsorbed monolayer on the treated surface.

In a particularly preferred embodiment, the unfolded protein is the same molecule as the therapeutic protein stored in the container. In this case, as the chaperone is chosen for having a good affinity with this protein, the chaperone will be very efficient for preventing aggregation. Moreover it facilitates the application of the invention to pharmaceutical formulations.

The efficiency of molecular linkers is illustrated by experimental results exposed below.

EXPERIMENTAL RESULTS

First Set of Experiments

Three plain borosilicate and three siliconized glass medical containers were filled with Human Insulin dissolved in a TRIS (trishydroxymethylaminomethane) buffer pH 7.25 (25 mM TRIS, 125 mM NaCl, 2 mM $MgCl_2$) at a final concentration of 0.5 mg/mL. The containers were then agitated at 60 rpm and 37° C. (up to t=2 H or t=16 H, depending of the experiment, according to the columns 2-3 and 5-6 of Table 1, below) which lead to the adsorption of insulin on the container surface. At the end of this pre-incubation step, solutions of insulin were removed and containers were washed with buffer to remove unabsorbed proteins.

A molecular chaperone protein was then added to the washed containers at least 15 min after.

The chosen chaperone is here the bacterial Hsp70 homologue DnaK from *Escherichia coli* but different molecular chaperones have been similarly tested: DnaJ, ClpB . . . and all can apply to the present invention. These families of proteins appear to exist in all living organisms, and can be produced in *Escherichia coli*, purified according to a known protocol developed by B. Bukau of the University of Heidelberg, and stored at −80° C.

As a "negative control", DnaK solution was also directly added to a fresh medical glass container filled with TRIS buffer pH 7.25 (25 mM TRIS, 125 mM NaCl, 2 mM MgCl2). This case corresponds to the other columns 1 and 4 of Table 1.

For each experiment, the amount of DnaK bound to the glass beads was then measured by SDS PAGE (PolyAcrylamide Gel Electrophoresis) after being washed with TRIS buffer and eluted with a buffer containing sodium docecyl sulfate (SDS). The electrophoresis is a method widely used for separating proteins according to their weight.

Figure 4:
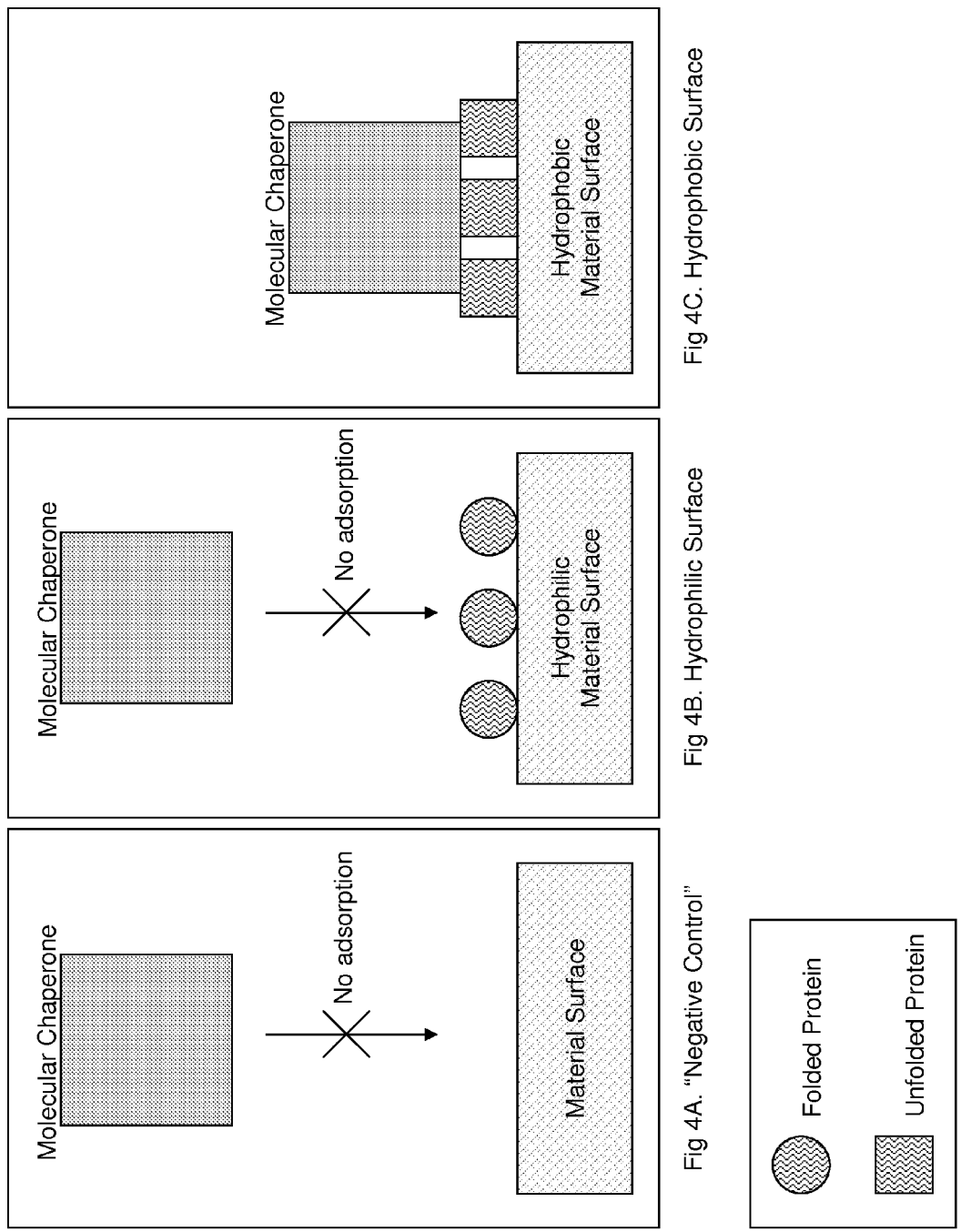
FIGS. 4A-C represents schematically the behaviour of chaperones in three experiments: without linker pre-adsorbed, with folded linker, and unfolded linker.

Each experiment was carried out in an identical manner. The obtained results are graphically represented in FIG. 4.

TABLE 1

| Pre-Incubation (Hours) | Borosilicate Glass Containers | | | Siliconized Glass Containers | | |
|---|---|---|---|---|---|---|
| | 0 | 2 | 16 | 0 | 2 | 16 |
| Amount of adsorbed insulin (µg) | 1 | 1 | 1 | 1 | 1 | 20 |
| Adsorbed DnaK (SDS PAGE) | − | − | − | − | + | ++ |

Increasing amounts
−
+
++

As expected, no DnaK could bind to the non-pre-incubated surfaces ("negative control", columns 1 and 4, Table 1), because there is no pre-adsorbed layer of insulin which can acts as a linker (FIG. 4A).

If the material used is plain borosilicate, inner surfaces are hydrophilic. And whatever the duration of pre-adsorption, adsorbed insulin stays folded and DnaK can not bind to the pre-incubated hydrophilic surface, as confirmed by the experiment (columns 2 and 3, Table 1). This result corresponds to the FIG. 4B.

Finally, a strong adsorption of DnaK on the pre-incubated hydrophobic surface is observed (columns 5-6, Table 1). Moreover, the longer the surface is pre-incubated (i.e the more insulin is adsorbed), the more DnaK bind the layer.

These experiments demonstrate the ability of DnaK, and other chaperones, to efficiently bind on material surface by the way of a molecular linker which is a pre-adsorbed and unfolded protein (FIG. 4C). The link created between the chaperone and the surface is strong enough to prevent release of the chaperones even if surfaces are washed again with a TRIS buffer.

Second Set of Experiments

Figure 5:
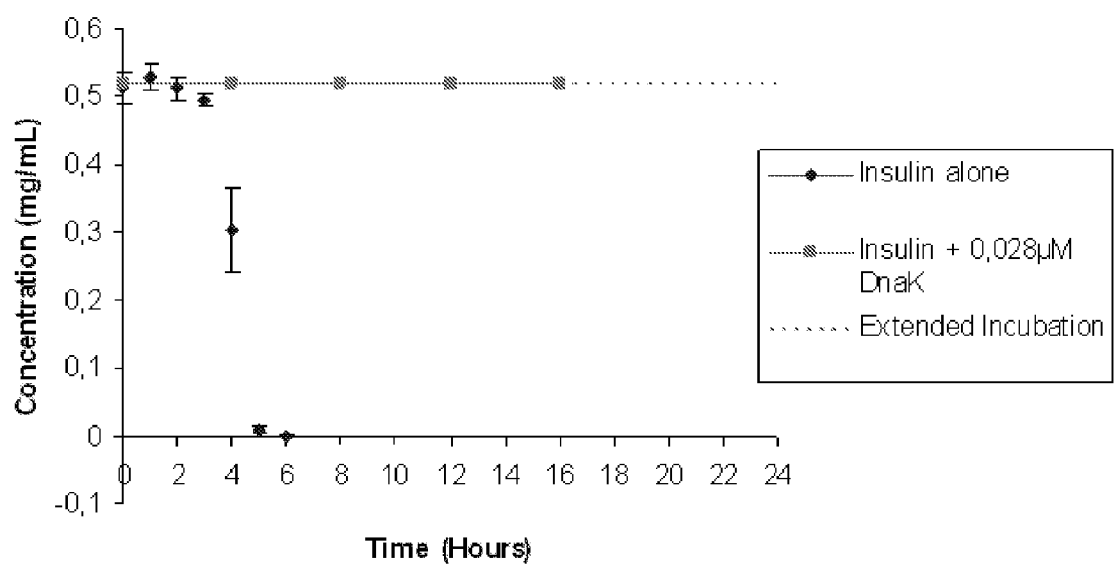
FIG. 5 represents graphically the evolution of the concentration of soluble insulin in a therapeutic solution during an experiment.

A subsequent experiment shows that linked chaperone keeps its efficiency. Concentration of remaining soluble insulin (unaggregated insulin) was monitored over time in a siliconized medical glass container coated with DnaK in the same conditions as the previous experiments, and then filled with a fresh insulin solution (86 µM). Results can be observed in FIG. 5.

In the case of insulin alone, its concentration falls after 2 h (the lag-time), whereas aggregation of insulin is prevented by the DnaK bound with a molecular linker. Thus, the chaperone is not altered by the molecular linker.

Other experimental data shows that the pre-adsorbed insulin layer preferably consists of approximately 1 µg of insulin on a total surface of 5 cm$^2$.

As the surface coverage of human insulin is approximately 1.5 mg/m$^2$, meaning 0.75 µg for 5 cm$^2$, the pre-adsorbed layer of insulin corresponds to a mixed (monomer/dimer/hexamer) monolayer of insulin on the surface. Its thickness is about a few nanometers (a mix of monomer/dimer/hexamer is about 3-5 nm, monomer alone is less than 1 nm).

The present invention may be useful for any container for holding a pharmaceutical solution, in particular, a solution containing protein. For example, the container may be a syringe, a cartridge, a vial, an ampoule, reservoir or other device or structure suitable for holding and containing a pharmaceutical compound. Aggregation of proteins is particularly problematic for syringes, as they are often treated either to facilitate gliding of the syringe plunger rod, to inhibit protein binding or to avoid leaches. Silicon oil, used as a lubricant to coat the sliding components of the syringe (the inside of the syringe barrel and the plunger stopper), is an apolar molecule that generates predominantly hydrophobic interactions which highly catalyze aggregation.

Another aspect of the present invention is directed to a method for coating the inner surface of a container with chaperones molecules. The inventive method follows the steps of the previously explained experience. It consists of filling the container with a solution containing a molecular linker, then emptying and washing it with a buffer after a first phase of pre-adsorption during which the linker begins to unfold, before finally adding to the inner surfaces of the container the chaperones molecules, which bind to the pre-adsorbed molecular linkers. Nucleation sites are blocked, and aggregation is prevented.

The invention claimed is:

1. A container containing a pharmaceutical solution containing a protein, said container having a hydrophobic inner surface and a coating thereon to isolate said pharmaceutical solution from said inner surface, said coating comprising:
    a linker adsorbed on said inner surface, wherein said linker comprises at least one of an unfolded protein, a carbohydrate, and a biological polymer; and
    a chaperone protein bound to said linker,
        wherein said chaperone protein stabilizes said linker in order to prevent aggregation of said protein.

2. The container according to claim 1, wherein said linker is the same molecule as said protein.

3. The container according to claim 1, wherein said linker defines a mixed monolayer of protein on the inner surface.

4. The container according to claim 3, wherein said monolayer has a thickness <5 nm.

5. The container according to claim 1, wherein the molar ratio of chaperone:linker is between 1:1 and 1:6000.

6. The container according to claim 1, wherein said linker is therapeutic insulin.

7. The container according to claim 1, wherein the container comprises one of a syringe, a cartridge, a vial, an ampoule, a reservoir or other device or structure suitable for holding and containing a pharmaceutical compound.

8. A method for coating the inner surface of a container with a coating comprising a linker and a chaperone protein bound to the linker, wherein the inner surface of the container is hydrophobic, comprising:
    filing the container with a solution containing a linker, wherein the linker comprises at least one of an unfolded protein, a carbohydrate, and a biological polymer;
    emptying the container after a time of pre-adsorption of said linker;
    washing the inner surfaces of the container with a buffer; and
    adding the chaperone protein to the container, thereby binding the chaperone protein to the linker.

9. The container according to claim 1, wherein said hydrophobic inner surface is silicone oil.

10. The container according to claim 1, where said hydrophobic inner surface is plastic.

11. The container according to claim 1, wherein said unfolded protein forms a monolayer.

12. The container according to claim 1, wherein said chaperone protein is at least one of DnaK, DnaJ, and ClpB.

13. The container according to claim 1, wherein the molar ratio of chaperone:linker is 1:300.

* * * * *